(12) United States Patent
Gusler

(10) Patent No.: US 7,090,548 B1
(45) Date of Patent: Aug. 15, 2006

(54) METHOD OF USING A LINEAR PROPULSOR ARRAY FOR PROPULSION AND NAVIGATION

(75) Inventor: Carl Phillip Gusler, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 11/050,593

(22) Filed: Feb. 3, 2005

(51) Int. Cl.
*B63H 1/30* (2006.01)
(52) U.S. Cl. .......................................... 440/16; 114/312
(58) Field of Classification Search ................ 114/312; 440/16; 5/600, 610
See application file for complete search history.

(56) References Cited

U.S. PATENT DOCUMENTS

| | | | | |
|---|---|---|---|---|
| 3,154,043 | A * | 10/1964 | Momsen, Jr. ................. | 440/16 |
| 3,221,702 | A | 12/1965 | Clark .............................. | 115/5 |
| 5,611,666 | A | 3/1997 | Au et al. ........................ | 416/82 |
| 5,820,342 | A | 10/1998 | Au et al. ........................ | 416/82 |
| 6,029,294 | A | 2/2000 | Saringer .......................... | 5/600 |
| 6,269,500 | B1 * | 8/2001 | Saringer ........................ | 440/16 |
| 6,561,479 | B1 | 5/2003 | Eldridge ........................ | 251/11 |
| 6,690,101 | B1 | 2/2004 | Magnussen et al. ......... | 310/328 |
| 6,702,734 | B1 | 3/2004 | Kim et al. .................... | 600/114 |
| 6,781,284 | B1 | 8/2004 | Pelrine et al. ............... | 310/330 |
| 2002/0156347 | A1 | 10/2002 | Kim et al. .................... | 600/160 |
| 2002/0173700 | A1 | 11/2002 | Kim et al. .................... | 600/114 |

OTHER PUBLICATIONS

Avron et al., "Swimming microbots: Dissipation, optimal stroke and scaling", at http://physics.technion.ac.il/~avron/files/pdf/optimal-swim-12.pdf. Mar. 25, 2004, (last visited Dec. 9, 2004).
Jon Edd et al., "Biomimetic Propulsion for a Swimming Surgical Micro-Robot," at http://www.me.cmu.edu/faculty1/sitti/nano/publications/iros03_last.pdf (last visited Dec. 8, 2004).
IBM Uncovers New Biomechanical Phenomenon, at http://domino.research.ibm.com/comm./pr.nsf/pages/news.20000414_fingers.html?Open&printable Apr. 14, 2000, (last visited Dec. 14, 2004).

\* cited by examiner

*Primary Examiner*—Lars A. Olson
(74) *Attorney, Agent, or Firm*—David A. Mims, Jr.; Rudolf D. Siegesmund

(57) ABSTRACT

The invention comprises a method of using a scalable, configurable "propulsor" system to move and navigate a submersible device through a fluid medium. A propulsor system is an assembly of individual propulsors that act in concert to form a substantially continuous control surface that undulates in a working fluid. Each propulsor is driven and configured by computer-controlled actuators so that the control surface undulates in various wave forms. Optional actuators that may refine the surface shape include an "orientation" actuator that drives rotation about the propulsor's longitudinal axis, and a "geometry" actuator that controls each propulsor's geometric configuration.

12 Claims, 13 Drawing Sheets

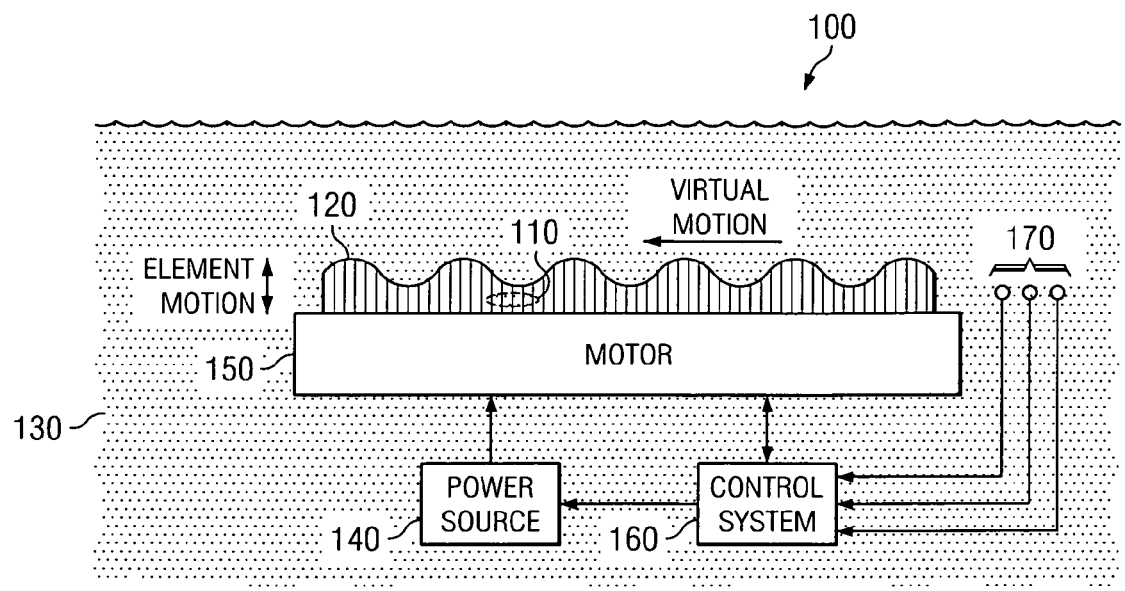
FIG. 1
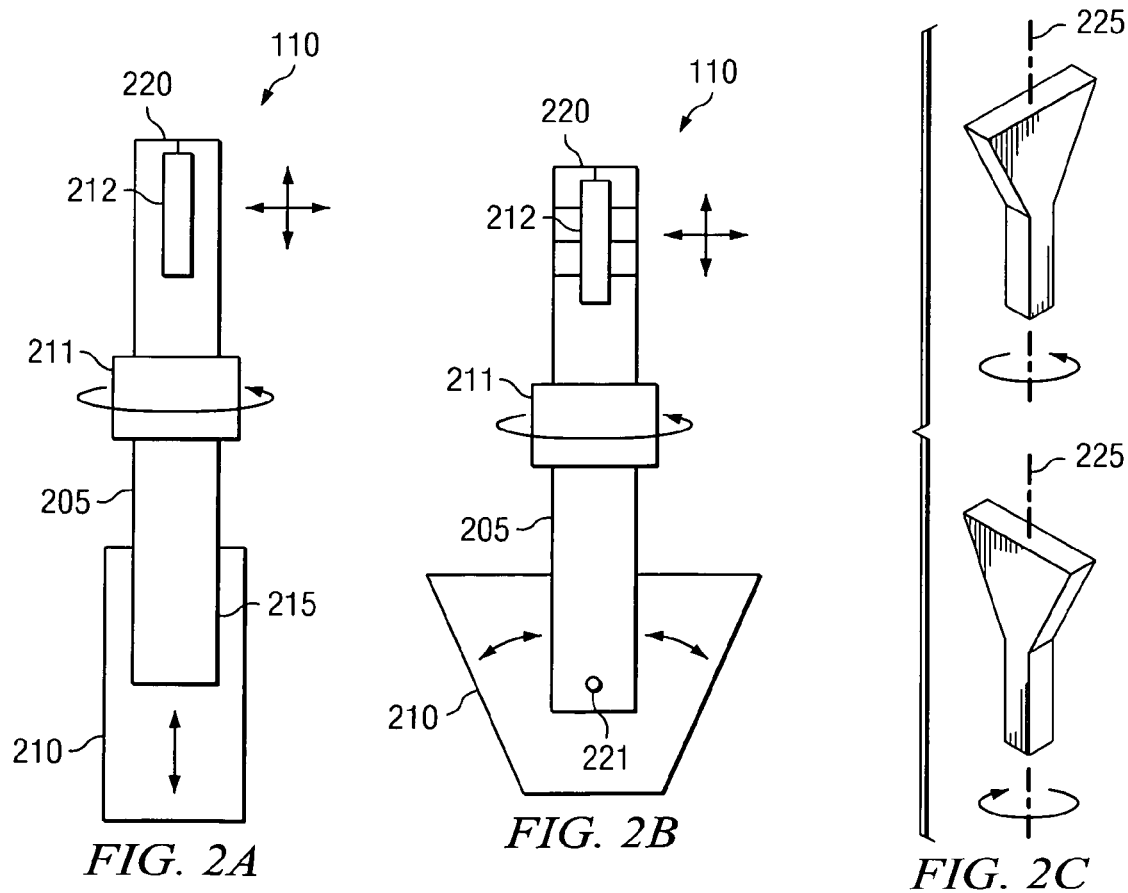
FIG. 2A
FIG. 2B
FIG. 2C

METHOD OF USING A LINEAR PROPULSOR ARRAY FOR PROPULSION AND NAVIGATION

CROSS-REFERENCE TO RELATED APPLICATION

The present invention is related to the subject matter of U.S. patent application Ser Nos. 11/050,601, 11/050,594 and 11/049,897 incorporated herein by reference.

FIELD OF THE INVENTION

The present invention generally is related to propulsion systems operable in a fluid medium, and, more specifically, to a method of using a traveling wave propulsion system move and navigate a submersible device through a fluid medium.

BACKGROUND OF THE INVENTION

Within the last hundred years, autonomous machines that perform useful tasks have emerged slowly from the realm of science fiction into a field of infinite practical application. More commonly known as "robots," such machines have been used for industrial automation, space exploration, and even cleaning house. Advances in robotics and miniaturization technology in recent years also have brought the possibility of micro-scale robots to the brink of reality. Combined with parallel advances in biotechnology, including the potential for DNA and other bio-molecules to provide power and control to artificial systems, see *IBM Uncovers New Biomechanical Phenomenon*, at http://domino.research.ibm-.com/comm/pr.nsf/pages/news.20000414_fingers.html?Open&printable (Apr. 14, 2000) (last visited Dec. 14, 2004) [hereinafter *Biomechanical Phenomenon*], such "micro-robots" could hold the key to new medical treatments. As noted by J. E. Avron et al. in *Swimming microbots: Dissipation, optimal stroke and scaling*, at http://physics.technion.ac.il/~avron/files/pdf/optimal-swim-12.pdf (Mar. 25, 2004) (last visited Dec. 9, 2004) [hereinafter *Swimming Microbots*], "The micron scale is sufficiently large to accommodate complex internal structures—a prerequisite to an autonomous smart device—and at the same time, is small enough to interface with functional microscopic biological systems." According to researchers at International Business Machines Corp. (IBM), micro-robots "could make it possible to determine on the spot if chest pain is caused by a heart attack or a more benign problem, saving time and potentially lowering treatment costs substantially." *Biomechanical Phenomenon*, supra. The researchers also envision a system for attacking cancerous growth: "the release of just the proper doses of chemicals in the appropriate location of the body could be achieved using tiny microcapsules equipped with nano-valves . . . . They could be programmed chemically to open only when they get biochemical signals from a targeted tumor type. This would enable the right therapy at the right place at the right time, with minimized side effects and no invasive surgery." Id. Others have proposed surgical micro-robots that "provide a novel and minimally invasive method of kidney stone destruction." See Jon Edd et al., *Biomimetic Propulsion for a Swimming Surgical Micro-Robot*, at http://www.me.cmu.edu/faculty1/sitti/nano/publications/iros03_last.PDF (last visited Dec. 8, 2004) [hereinafter *Biomimetic Propulsion*].

But developing micro-robots for biological applications is replete with novel challenges, not the least of which is developing a biologically safe propulsion system that can operate while submersed in unusual fluid media—such as blood, saliva, or even spinal fluid—at the micron scale. Edd et al. propose a propulsion system for their swimming surgical micro-robot that mimics the natural propulsion systems of bacteria and spermatozoa. *Biomimetic Propulsion*, supra. Bacteria locomotion is, of course, particularly adapted to the viscous fluids in found in biological systems. Id. For these systems, which rely on flagella and cilia to swim, propulsion is achieved through "effective use of the viscous drag produced from the spinning tail . . . . Whereas typical motors exhibit undesirable effects due to the increased influence of viscosity, flagella and cilia depend completely on this to function." Id. Thus, Edd et al. proposes to use carbon nanotubes to create synthetic flagella, which propel the micro-robot. Id. Carbon nanotubes, according to Edd et al., are an ideal choice inasmuch as they are "sufficiently elastic to allow easy conformation into a helical shape when revolved in a viscous medium" and have "relatively non-reactive surfaces with strong covalent bonds to minimize any degradation caused by the biological surroundings." Id. Carbon nanotubes also can be fabricated at the micron scale in relatively short time. Id. But as the authors confess, "This system contains components of many different scales, significantly increasing the difficulty of fabrication." Id. Moreover, while theoretically provocative and ostensibly safe to biological systems, the system proposed by Edd et al. is unproven and, thus, potentially unreliable.

Of course, marine propulsion systems have been developing for centuries—from oars and sails to jet devices and nuclear drives. On large marine vessels, the screw propeller is probably the most common propulsion device, but centrifugal pumps also are frequently used to move a vessel through water. Lesser known alternatives to propellers and pumps, though, have been inspired by the naturally efficient propulsion systems of fish and other marine life. In 1964, for instance, the United States Patent & Trademark Office issued a patent for a "Hydrodynamic Traveling Wave Propulsion Apparatus," which purports to simulate "the undulating motion made by the body of a swimming fish." U.S. Pat. No. 3,154,043 (issued Oct. 27, 1964). Other notable devices include an "Undulating Surface Driving System," U.S. Pat. No. 3,221,702 (issued Dec. 7, 1965), a "Mechanism for Generating Wave Motion," U.S. Pat. No. 6,029,294 (issued Feb. 29, 2000), and a "Fluid Forcing Device," U.S. Pat. No. 5,611,666 (issued Mar. 18, 1997); see also U.S. Pat. No. 5,820,342 (issued Oct. 13, 1998) (a "Fluid Forcing Device with a Fluted Roller Drive"). These propulsion systems are described in more detail below, but in general, each of these systems includes an undulating control surface that interacts with the surrounding fluid (water) to produce reactionary forces that propel a vessel through the fluid.

The '043 patent, issued to Charles Momsen, Jr. discloses a traveling wave propulsion system mounted on a submarine. Momsen's propulsion system comprises a variable-speed motor that drives a plurality of valves, which, in turn, control the expansion or contraction of a plurality of expandable "members or cells" mounted on the hull and enclosed in flexible elastic membranes. Each valve causes a cell to expand and contract in "timed relation" to other cells, thus expanding and contracting a portion of a membrane during each revolution of the valve so that the membrane "is manipulated substantially in the shape of a traveling sine wave, the wave traveling along the length of the membrane in continuous repetition as long as the mechanism is operated." The undulating membranes react with the surrounding water to provide propulsive forces to the vessel. For a single vessel, Momsen indicates that a plurality of such propulsion devices "are mounted equidistantly around the circumference of the submarine." Generally, each propulsion device is oriented lengthwise along the hull. Momsen further discloses a basic control system, in which the "traveling sine wave" travels from bow to stern for forward motion, and from stern to bow for reverse motion. Lateral control is provided by operating membranes on only one side of the vessel. Similarly, vertical control is provided by operating membranes on either the top or bottom of the vessel.

The '702 patent, issued to Chester A. Clark, describes a similar device for propelling torpedoes, submarines, or other cylindrical-shaped vessel. The inner surface of the cylindrical body is provided with "a plurality of axially aligned tubular openings that serve as bearing surfaces for elongated rotary valves inserted into the tubular openings." The cylindrical body also comprises "equally spaced axially aligned apertures through the surface thereof meeting with the elongated tubular openings to permit fluid flow through the valves and through the aperture in the body." Alternating valves permit expansion and contraction of an expansible material in timed relationship. Contraction of the expansible material is produced by the pressure of the surrounding water, which acts against the fluid pressure within the expansible covering. Thus, the expansible covering under the influence of the pressure pump and the surrounding pressure takes the shape of a sine-like wave that travels along the length of the body. The motion provides propulsion to the vessel or device. Unlike Momsen's device, though, Clark's device comprises a single flexible membrane that encompasses the entire vessel.

The '294 patent, issued to John H. Saringer, describes another apparatus for generating wave motion that "can be adapted for numerous applications including . . . propulsion systems." Like Momsen and Clark, Saringer discloses an apparatus having a "flexible" member driven by mechanical means to create a traveling wave form. Saringer describes the mechanical means for driving the flexible member as an apparatus comprising a crank assembly mounted on a frame, with the crank assembly having an axis of rotation and being rotatable about the axis of rotation. The apparatus includes at least two beams, each beam having "at least one crank attachment position radially offset from the axis of rotation and being attached to the crank assembly at the crank attachment position." The crank attachment positions are offset from each other by "a pre-selected angular displacement." Thus, each beam oscillates in a plane when the crank assembly is rotated, and produces a traveling wave in the flexible member.

The '666 patent, issued to Ching Y. Au, discloses yet another recent embodiment traveling wave systems. Au's "fluid forcing device," though, departs from the "flexible membrane" approach. Instead, Au's device comprises a "multiplicity of elements rotating around a central axle," arranged in such a way that the ends of the elements form a pre-determined wave. Each element has a solid composite type of anti-friction bearing that also serves to maintain a small clearance between adjacent elements. The clearance between elements is just big enough to prevent rubbing between elements, but small enough to act as a "dynamic seal" between elements (thus obviating the need for a flexible membrane).

The conventional propulsion systems described above typically are powered with a variety of motors, including steam turbines, gas turbines, combustion engines, or electric motors. But converting such devices into micro- or nano- scale devices for biological applications is problematic. Propellers and pumps, for instance, generally require bearings and seals that are difficult to manufacture or assemble at such small scales. Propellers and pumps also are a potential hazard to delicate biological systems, and additional care must be taken when designing systems for biological applications. Pumps, in particular, are susceptible to taking in and destroying objects from surrounding fluid. And while propellers are vulnerable to damage from foreign objects in a fluid, the more significant concern in a biological application is the potential damage that a propeller could cause to objects in or bounding the fluid. The alternative undulating surface systems described above, though, pose no such risks in biological applications. Thus, what is needed is such a system that can be assembled and can operate on the micron scale.

SUMMARY OF THE INVENTION

The invention described in detail below comprises a method of using a scalable, configurable "propulsor" system to move and navigate a submersible device through a fluid medium. A propulsor system is an assembly of individual propulsors that act in concert to form a substantially continuous control surface that undulates in a working fluid. Each propulsor is drive and configured by computer-controlled actuators so that the control surface undulates in various wave forms. Optional actuators that may refine the surface shape include an "orientation" actuator that drives rotation about the propulsor's longitudinal axis, and a "geometry" actuator that controls each propulsor's geometric configuration.

BRIEF DESCRIPTION OF DRAWINGS

The novel features believed characteristic of the invention are set forth in the appended claims. The invention itself, however, as well as a preferred mode of use, further objectives and advantages thereof, will be understood best by reference to the following detailed description of an illustrative embodiment when read in conjunction with the accompanying drawings, wherein:

DETAILED DESCRIPTION OF THE PREFERRED EMBODIMENT

The invention described herein comprises a "linear propulsor array," which acts upon any working fluid to cause a reactive force. Mounted on a mobile device, a linear propulsor array generates a reactive force in the working fluid that propels the device through the fluid. Alternatively mounted on a stationary platform, a linear propulsor array generates a reactive force that drives the fluid surrounding the array.

Figure 6A:
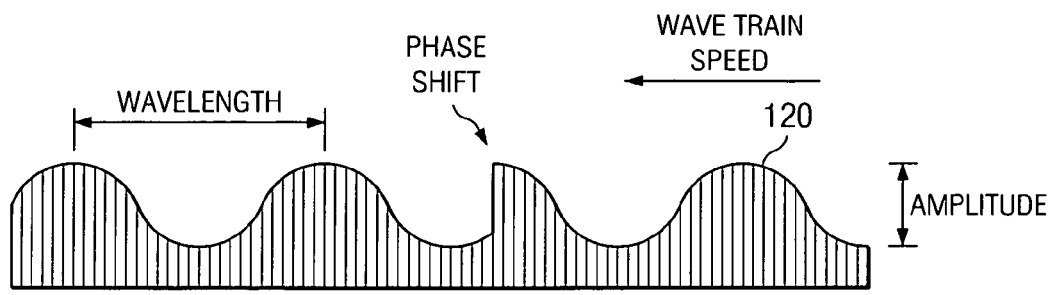
FIG. 6 illustrates various wave forms that the control system can generate on a propulsor array control surface.
Figures 1, 6B:
FIG. 1 illustrates broad features of an exemplary propulsor array.

FIG. 1 highlights some of the broad features of an exemplary linear propulsor array. Linear propulsor array 100 is an assembly of individual "propulsors" 110 that act in concert to form a substantially continuous control surface 120 that undulates in working fluid 130. Propulsor array 100 is powered by power source 140 and driven by motor 150 under the control of control system 160, which receives data from various sensors 170. A propulsor 110 generally comprises a bar 205 and a primary actuator 210 coupled to bar 205 on base 215, as shown in FIG. 2A.

Bar 205 generally is a straight, substantially rigid piece of material having a control tip 220 opposite primary actuator 210. Although bar 205 may have a variety of cross-sections, which may be solid, hollow, symmetric, or asymmetric, bar 205 is preferably a solid rod having a square or circular cross-section for easy assembly and efficient packing.

Primary actuator 210 moves bar 205 in order to impart energy to the working fluid. In one embodiment, primary actuator 210 reciprocates bar 205 in a linear motion as shown in FIG. 2A. Depending upon the composition of working fluid 130, though, propulsor 110 may operate more effectively at an angle. In an alternative embodiment, primary actuator 210 rotates bar 205 in a radial motion about pivot 221 in a radial motion, as shown in FIG. 2B. Generally, such a radial motion maximizes energy in one part of the cycle, which is analogous to paddling a canoe.

Figure 2D:
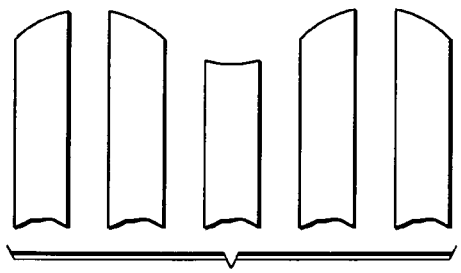
FIG. 2D illustrates the operation of an optional geometry actuator.

FIG. 2C also depicts an optional "orientation" actuator 211 and an optional "geometry" actuator 212, either or both of which can be used to refine the shape of control surface 120. Orientation actuator 211 generally rotates an individual propulsor 110 about axis 225, as FIG. 2C illustrates. Orientation actuator 211 may be integrated with primary actuator 210 and coupled to bar 205 at base 215, or may be an independent mechanism coupled to bar 205 at any functional position. Geometry actuator 212 changes the shape of propulsor 110 by altering the configuration of control tip 220. FIG. 2D illustrates how geometry actuator 212 may extend or retract control tip 220 so that the shape of bar 205 refines the shape of undulating control surface 120. FIGS. 2E through 2I depict geometry manipulation that is useful particularly with radial motion to increase or decrease drag as needed.

Figure 2E:
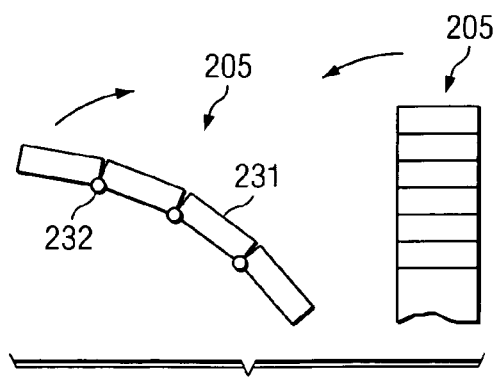
FIGS. 2E–2I depict useful geometry manipulations.

In FIG. 2E, bar 205 is constructed so that its rigidity can be changed. During the "power" part of the movement cycle, bar 205 is rigid. During the "return" part of the movement cycle, bar 205 is flexible and flexed, thus reducing its profile and its drag in working fluid 130. Variable rigidity can be provided by a number of mechanical means. In this embodiment, variable rigidity is provided by building bar 205 out of segments 231 that are connected by hinges 232, and locking or releasing hinges 232 through the action of geometry actuator 212 at appropriate points in the cycle.

Figure 2F:
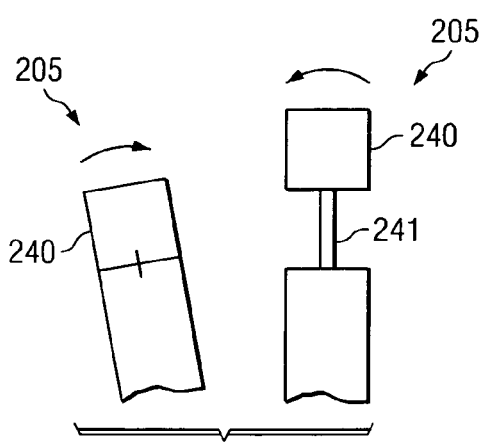

FIG. 2F depicts bar 205 constructed so that its length can be changed. During the "power" part of the movement cycle, segment 240 is extended. During the "return" part of the movement cycle, segment 240 is retracted, thus reducing the profile and drag of propulsor 110 in fluid 130. Variable length can be provided by a number of mechanical means. In this embodiment, variable length is provided by building bar 205 with rod 241 and segment 240 and extending or retracting segment 240 via rod 241 through the action of geometry actuator 212 at appropriate points in the cycle.

Figure 2G:
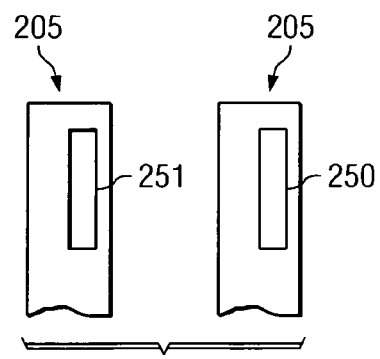

FIG. 2G depicts bar 205 constructed so that its cross-section can be varied. During the "power" part of the movement cycle, the cross-section of bar 205 is maximized. During the "return" part of the movement cycle, the cross-section of propulsor 110 is minimized, thus reducing its drag in fluid 130. In this embodiment, variable cross-section is provided by moving cover 250 through the action of geometry actuator 212 to open and close one or more openings 251 within bar 205.

Figure 2H:
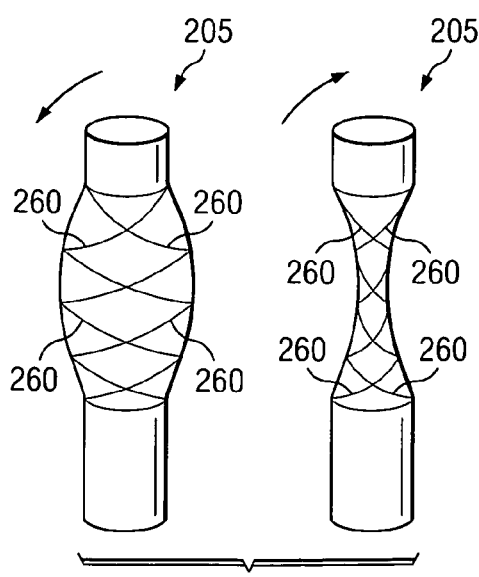

FIG. 2H depicts bar 205 constructed so that its shape can be altered. In this embodiment, controlled fibers 260 expand or compress a portion of bar 205 through the action of geometry actuator 212 at appropriate points in the back-and-forth cycle to increase and reduce drag, respectively.

Figure 2I:
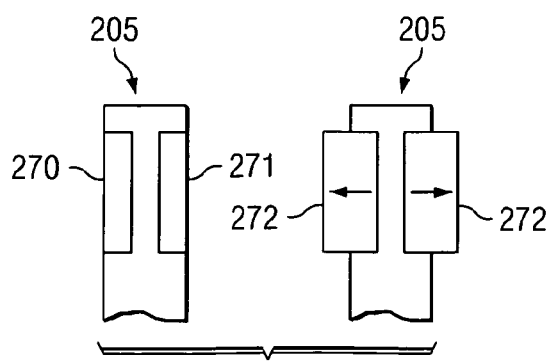

FIG. 2I depicts bar 205 constructed so that its width can be changed. During the "power" part of the movement cycle, bar 205 is widened. During the "return" part of the movement cycle, bar 205 is narrowed, thus reducing its profile and its drag in fluid 130. Variable width can be provided by a number of mechanical means. In this embodiment, variable width is created by providing bar 205 slots 270 and 271 in opposing sides, and extending or retracting covers 272 through the action of geometry actuator 212 at appropriate points in the back-and-forth cycle.

Figure 3A:
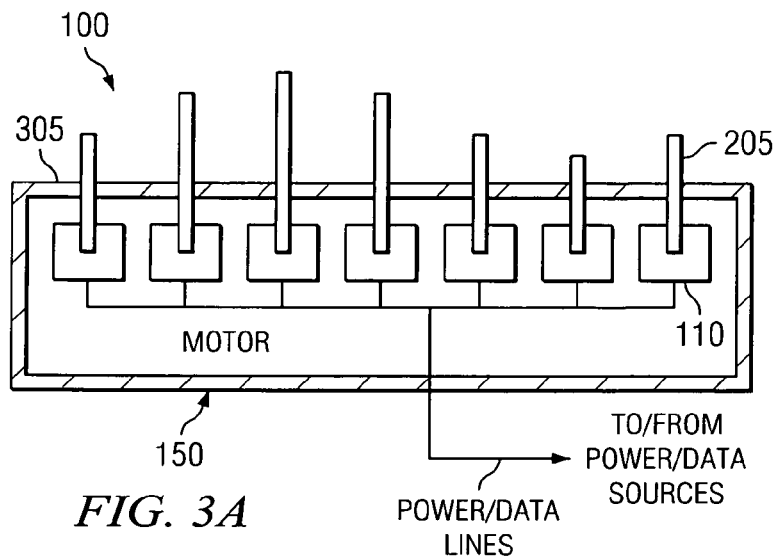
FIG. 3 is a detailed view of a motor that drives a propulsor array.
Figure 3B:
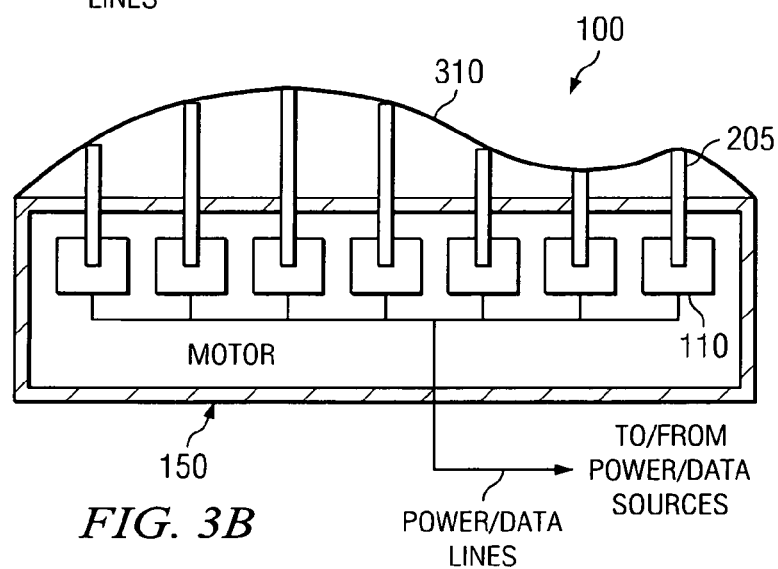
Figure 3C:
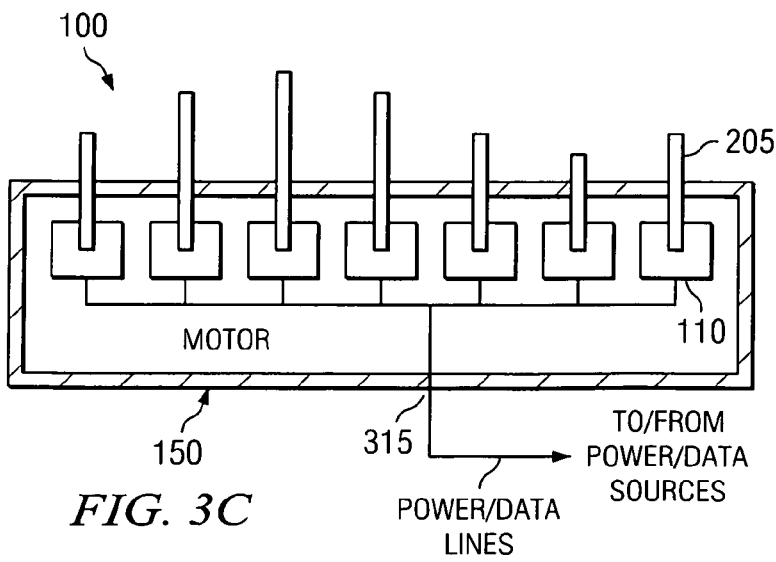

FIGS. 3A through 3C provide a more detailed view of motor 150 that drives propulsor array 100. Inasmuch as propulsor array 100 is intended to operate while submersed in working fluid 130, means are provided for protecting propulsor array 100 and motor 150 from any harmful effects of working fluid 130. FIG. 3A illustrates a simple means wherein bars 205 are exposed directly to the fluid, but seal 305 between bars 205 and motor 150 prevent working fluid 130 from entering motor 150. FIG. 3B illustrates an alternative means wherein a flexible material 310 covers the entire propulsor array 100, protecting propulsor array 100 and motor 150 from working fluid 130. Of course, there may be applications where it is advantageous to allow working fluid 130 to flood motor 150. For example, some types of working fluid 130 may provide some lubrication and cooling benefits to motor 150 without disrupting the efficiency of propulsor array 100. Moreover, for many biological applications, propulsor array 100 and motor 150 may be part of a disposable device, in which case any long-term corrosive effects are unimportant. If motor 150 is mounted on a platform or device, such as the hull of a submarine, seal 315 between motor 150 and the platform allow data and power lines to feed propulsor array 100 without fluid leaking into the supporting platform, as seen in FIG. 3C.

The technology and scale of primary actuator 210, motor 150, and optional actuators 211 and 212 varies according to the scale of bar 205. For example, if mounted on a large freight ship, such components likely would be driven by hydraulic fluid or compressed air. On a small boat, electric solenoids likely are a better choice. For micro- or nano-scale applications, motor 150 and actuators 210–212 may be driven by piezoelectric power, or even bio-mechanical sources.

Figure 4A:
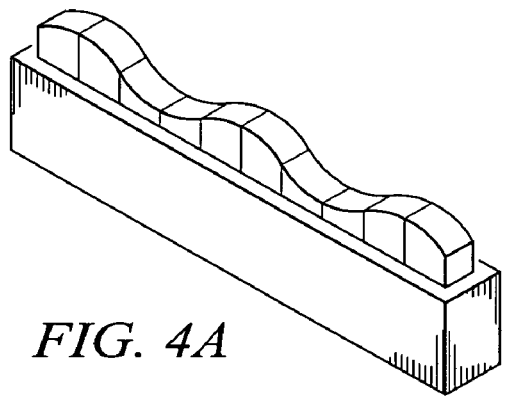
FIG. 4 illustrates alternative configurations of a propulsor array.
Figure 4B:
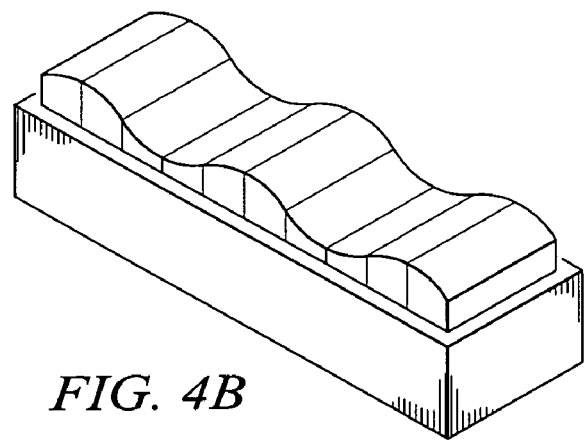
Figure 4C:
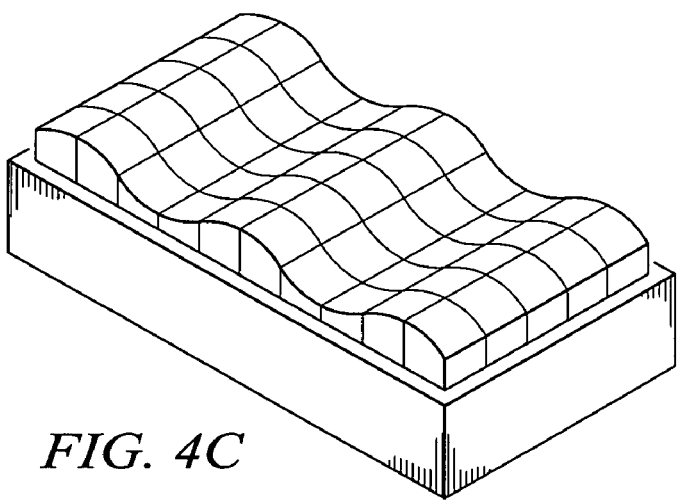

FIGS. 4A through 4C illustrate several alternative configurations of propulsor array 100. In FIG. 4A, propulsor array 100 forms a relatively thin strip, in which each control tip 220 has a square or circular geometry. In FIG. 4B, propulsor array 100 forms a wider strip, in which each control tip 220 has a rectangular or elliptical geometry. In FIG. 4C, several thin strips are assembled close together, forming a wide strip that can undulate in two dimensions rather than just one.

Figure 5:
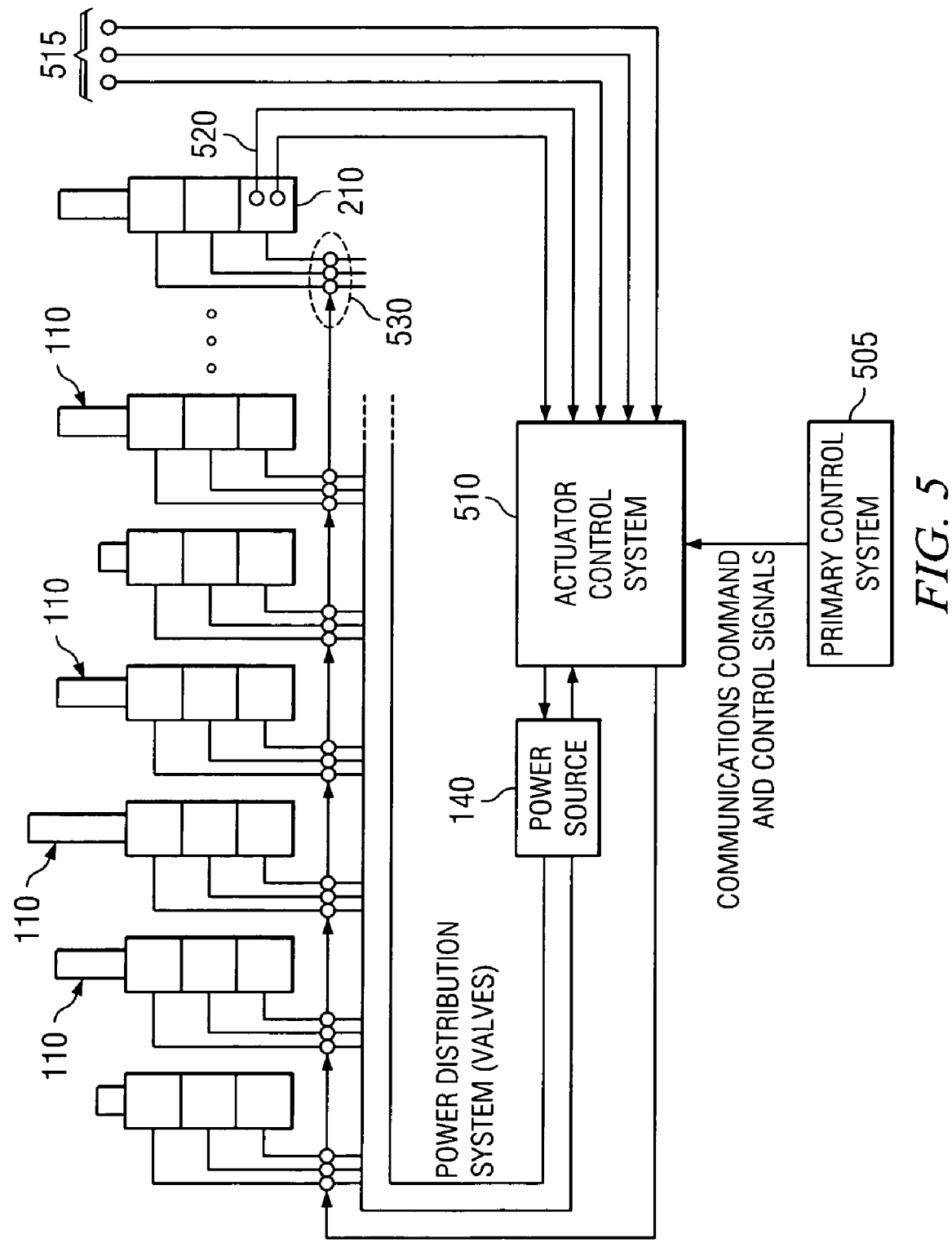
FIG. 5 illustrates the relationships between a propulsor control system and other propulsor components.

FIG. 5 provides a more detailed perspective of the relationship between control system 160 and other components of propulsor array 100. Generally, control system 160 comprises primary control system (PCS) 505 and actuator control system (ACS) 510. ACS 510 primarily is responsible for determining the appropriate shape of control surface 120 for any given objective, and for manipulating each control tip 220 to create the appropriate control surface 120. Sensors 170 provide necessary data to ACS 510. Sensors 170 generally comprise external sensors 515 and internal sensors 520. Internal sensors 520 embedded in actuators 210, 211, 212, or motor 150 provide operational information, such as temperature, pressure, and power flow. Internal sensors 520 also may provide diagnostic information, such as identification of failing actuators. External sensors 515 exposed to working fluid 130 provide environmental information, such as fluid temperature, pressure, or velocity, and chemical information, such as pH, viscosity, ionization, or solubility. ACS 510 also receives and processes major command and control signals from PCS 505, including guidance and navigation commands such as "start," "stop," "accelerate," or the like. Power is distributed from power source 140 to each propulsor 110 via gates 530. The type of power determines the appropriate type of gate, but gates 530 are likely to be valves or switches. The opening and closing of gates 530 is directly controlled by ACS 510. ACS 510 creates the appropriate control surface 120 by choreographing the opening and closing of all power distribution gates 530. ACS 510 also controls the general operations of power source 140, such as start up, shut down, increase available power, etc. ACS 510 receives important status information from power source 140, such as total power output and fuel consumption.

The following discussion and accompanying figures describe the various wave forms that ACS 510 can generate on control surface 120, as well as the advantages of each over prior art wave generating systems.

ACS 510 is capable of generating a "wave train" across control surface 120, as FIG. 6A illustrates. FIG. 6A shows the standard dimensions of a "wave train" of a given wavelength and amplitude that propagates across control surface 120. Unlike standard waves in familiar media (such as sound waves, light waves, and most ocean waves), ACS 510 is capable of generating waves where the wave train speed is independent of the wavelength. In other words, a wave train with a wavelength of 1 inch could have a wave train speed of one inch per second, one inch per minute, or one inch per millisecond. FIG. 6A also shows a discontinuity in the wave train, in this case a shift in the phase of the waves from one portion of control surface 120 to another. This phase shift could be propagated down control surface 120, but most likely would represent a discontinuity in control surface 120. Wave behavior to the left of the discontinuity point may be different than to the right of the point. This would enable ACS 510 to generate different kinds of thrust on one end of propulsor array 100 than the other end. This may be useful for braking, and would be most useful for orienting propulsor array 100 in the surrounding fluid.

Figures 2, 6B:
FIG. 2A illustrates the components of an individual propulsor.
FIG. 2B illustrates an alternative embodiment of a propulsor.
FIG. 2C illustrates the operation of an optional orientation actuator.
Figures 3, 6B:

ACS 510 also can generate different wave shapes across control surface 120, as FIGS. 6B-1 through 6B-3 illustrate. In FIGS. 6B-1 and 6B-2, for example, the wave is sinusoidal and saw-toothed, respectively. Different fluids with different characteristics (such as viscosity or high concentrations of floating objects) may require different wave shapes. Even the same fluid may require different wave shapes depending on the objective of motion. When starting, accelerating, or braking, the wave shape will need to generate maximum "bite" into the fluid and maximize power transfer to the fluid. This will require not only increased wave amplitude, but wave shapes that convey maximum power to the fluid. When coasting through the fluid at cruising speed, the wave shape will need to be streamlined to minimize drag, but have enough amplitude to maintain speed and inertia. FIGS. 6B-3 is an example of a wave having multiple, random shapes that can generate maximum turbulence in a fluid, when desired.

Figure 6C:
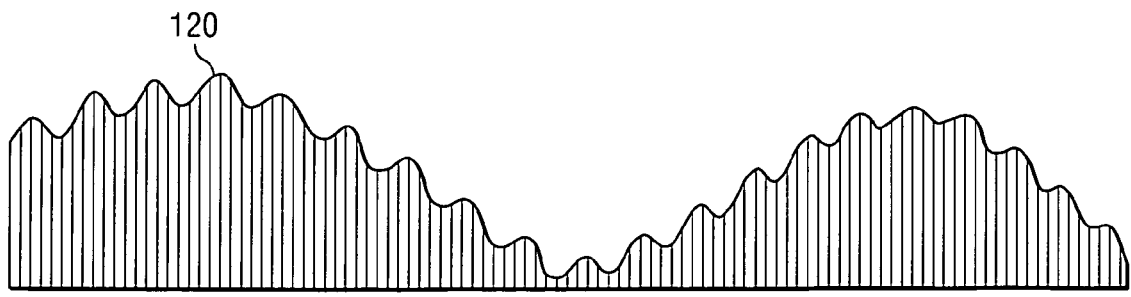

ACS 510 also has the capacity to generate different simultaneous wave shapes across control surface 120, as FIG. 6C illustrates. In FIG. 6C, a primary wave is modulated with a secondary wave having a shorter wavelength and low amplitude. These two simultaneous wave shapes can travel at different speeds and different directions to increase drag or power, or a new wave form can start out with small amplitude and gradually increase to make a smooth transition from one operation to another.

As ACS 510 receives command and control instructions from PCS 505, ACS 510 chooses from the various techniques, described above and illustrated in FIG. 6, to select the best method for achieving results, which may include attempting to maximize power transmission, minimize drag, maintain laminar flow, add turbulence, or the like. ACS 510 evaluates results using internal sensors 520 and external sensors 515. Those skilled in the art will appreciate that ACS 510 also may employ expert systems, experimentation, and learning techniques to determine the most economical way to achieve results, by measuring results in the velocity, pressure, and temperature of the resulting fluid flow and comparing the results with the power required to generate that result. Moreover, ACS 510 may have preprogrammed methods for specific fluid situations (temperature, viscosity, etc.), or can experiment to directly determine best methods for current circumstances. For example, in a biological application a robot micro-submarine may move through different kinds of environments, such as an artery, lymph node, bladder, or the like, and may encounter different kinds of fluids in each of these environments, such as blood, spinal fluid, lymph, or the like. For such an application, ACS 510 may be preprogrammed to use certain wave characteristics for specific fluids. In contrast, a similar device deployed within a sewer system may need to move through many unknown and unexpected kinds of fluids, such as water, gasoline, motor oil, or the like. Thus, in this latter scenario, ACS 510 may be programmed to test different wave characteristics to determine the characteristics that best serve current (and changing) conditions.

As noted at the outset, a propulsor array such as propulsor array 100 mounted on a mobile device can propel the device through a fluid. Moreover, combined with control system 160, such a device can achieve autonomous navigation. Alternatively, propulsor arrays 100 similarly could be placed on the inside of a hollow cylindrical body, such as a pipe, in order to move fluid inside the pipe, or to move or orient objects in the fluid inside the hollow body. A person of ordinary skill in the art should appreciate that applications for such a combination are virtually endless, but certain techniques for using control system 160 to navigate are described below with reference to a simple embodiment wherein the mobile device is a solid cylindrical body, representative of the hull of a ship or submarine, as illustrated in FIG. 7.

Figure 7A:
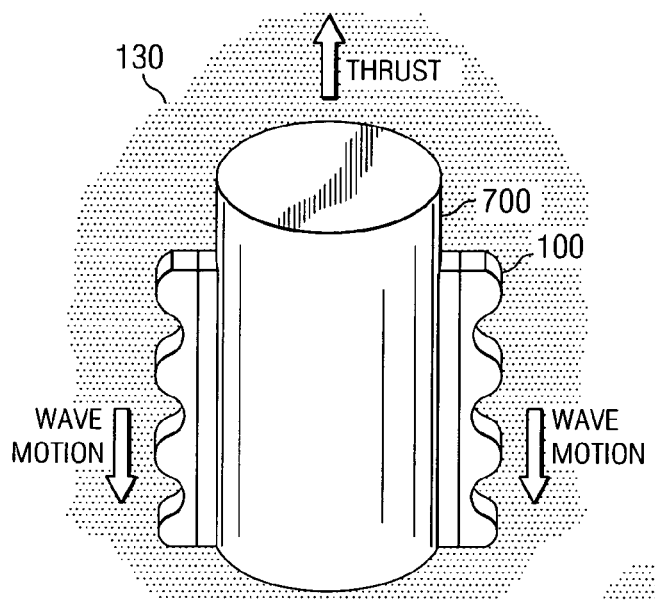
FIG. 7 illustrates techniques for using the control system to navigate a simple submersible device.
Figure 7B:
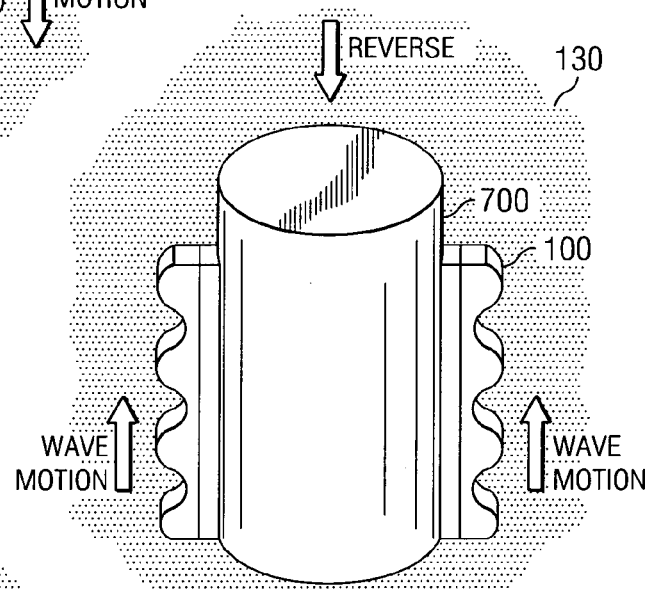
Figure 7C:
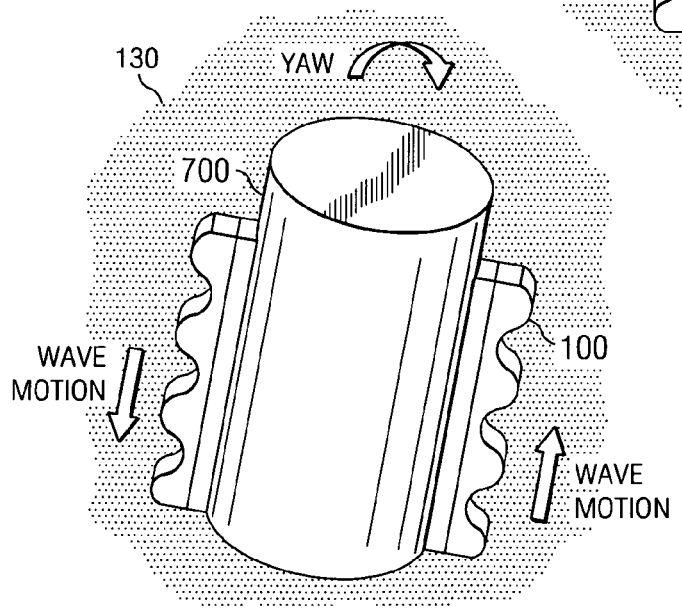

In FIGS. 7A through 7C, propulsor arrays 100 are installed in complementary opposing pairs on submersible device 700. As FIG. 7A illustrates, the downward motion of propulsor arrays 100 induces a downward motion in the surrounding fluid 130, thus providing upward thrust to device 700. Conversely, in FIG. 7B, the upward wave motion of both propulsor arrays 100 induces an upward motion in the surrounding fluid, thus providing downward thrust to device 700. In FIG. 7C, each propulsor array 100 in the pair is generating a wave motion in the opposite direction relative to its compliment, thus providing a sideways force and a yaw motion to device 700. Note that propulsor arrays 100 mounted on the "top" and "bottom" of device 100 could generate additional thrust, as well as a sideways force that could provide a pitch motion to device 100. Propulsor arrays also can generate other combinations of forces on device 100 by generating complex wave shapes on the various control surfaces 120. For example, both thrust and yaw could be generated simultaneously.

Figure 7D:
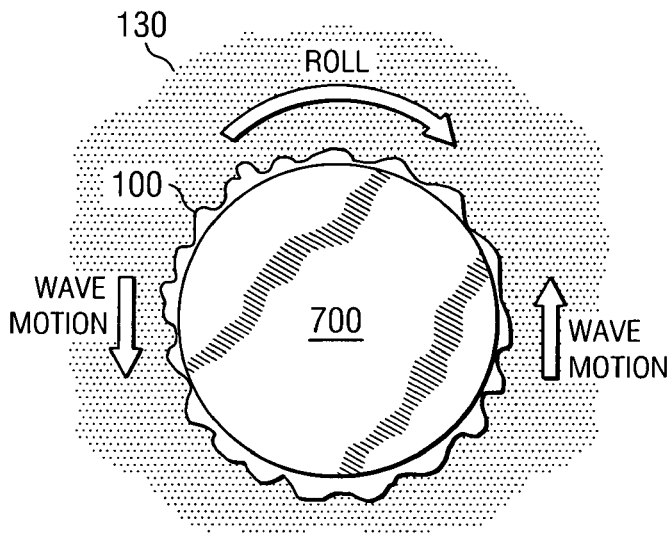
Figure 7E:
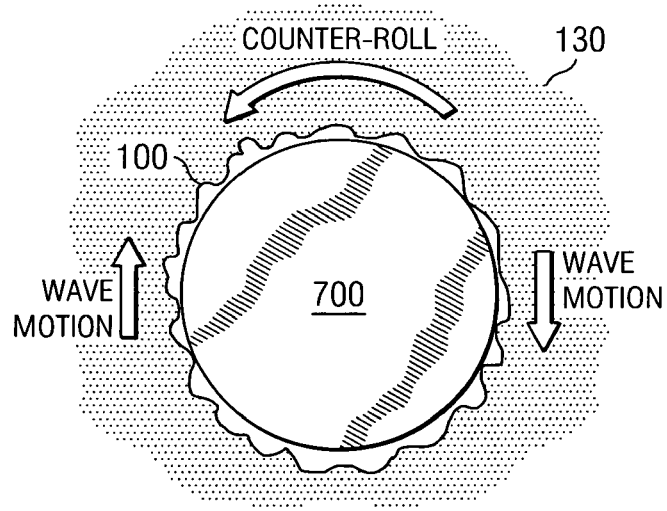
Figure 7F:
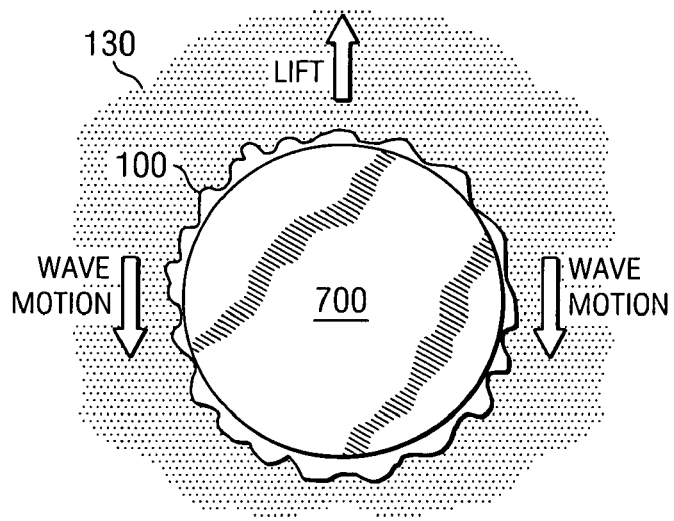

FIGS. 7D through 7F illustrate the cross-section of device 700, in which a single propulsor array 100 is installed around the circumference of device 700. In FIG. 7D, the counter-clockwise wave motion of propulsor array 100 induces a counter-clockwise motion in the surrounding fluid, thus providing clockwise thrust or rolling motion to device 700. Conversely, in FIG. 7E, the clockwise wave motion of propulsor array 100 induces a clockwise motion in the surrounding fluid, thus providing counter-clockwise thrust or rolling motion to device 700. FIG. 7F illustrates the motion of discontinuous control surface 120, in which both halves generate downward wave motion, thus producing a lifting force on device 700. Additional propulsor arrays 100 mounted along the length of device 700 could generate additional thrust, as well as a sideways force to provide a rolling motion to device 700 in the other dimension (or in a combination of both dimensions). And as noted above, propulsor arrays also can generate other combinations of forces on device 100 by generating complex wave shapes on the various control surfaces 120. For example, both roll and lift could be generated simultaneously.

Figure 8A:
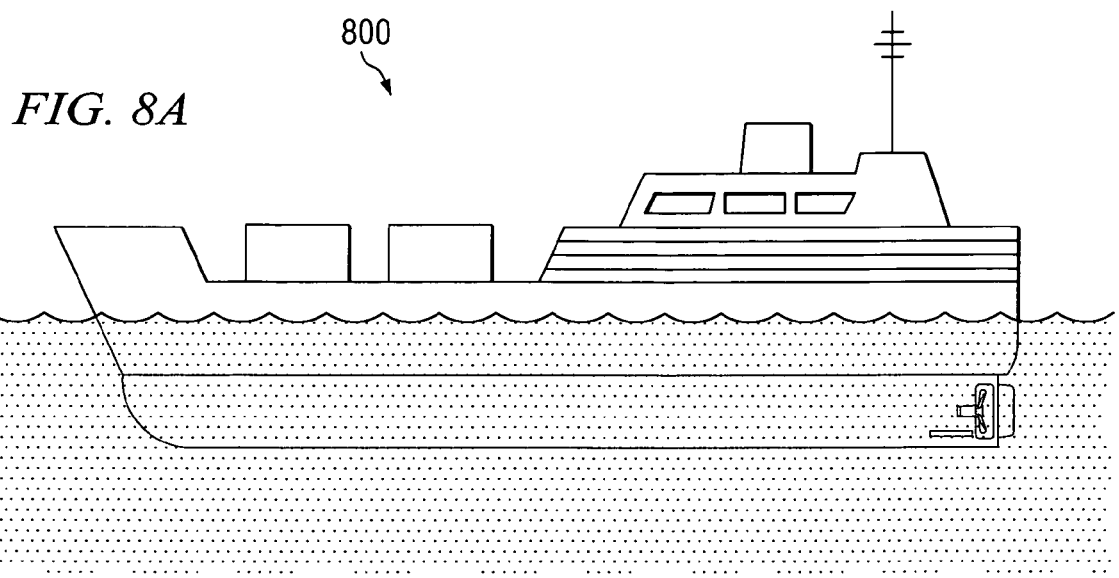
FIG. 8 illustrates an application of a propulsor array to large marine vessels.
Figure 8B:
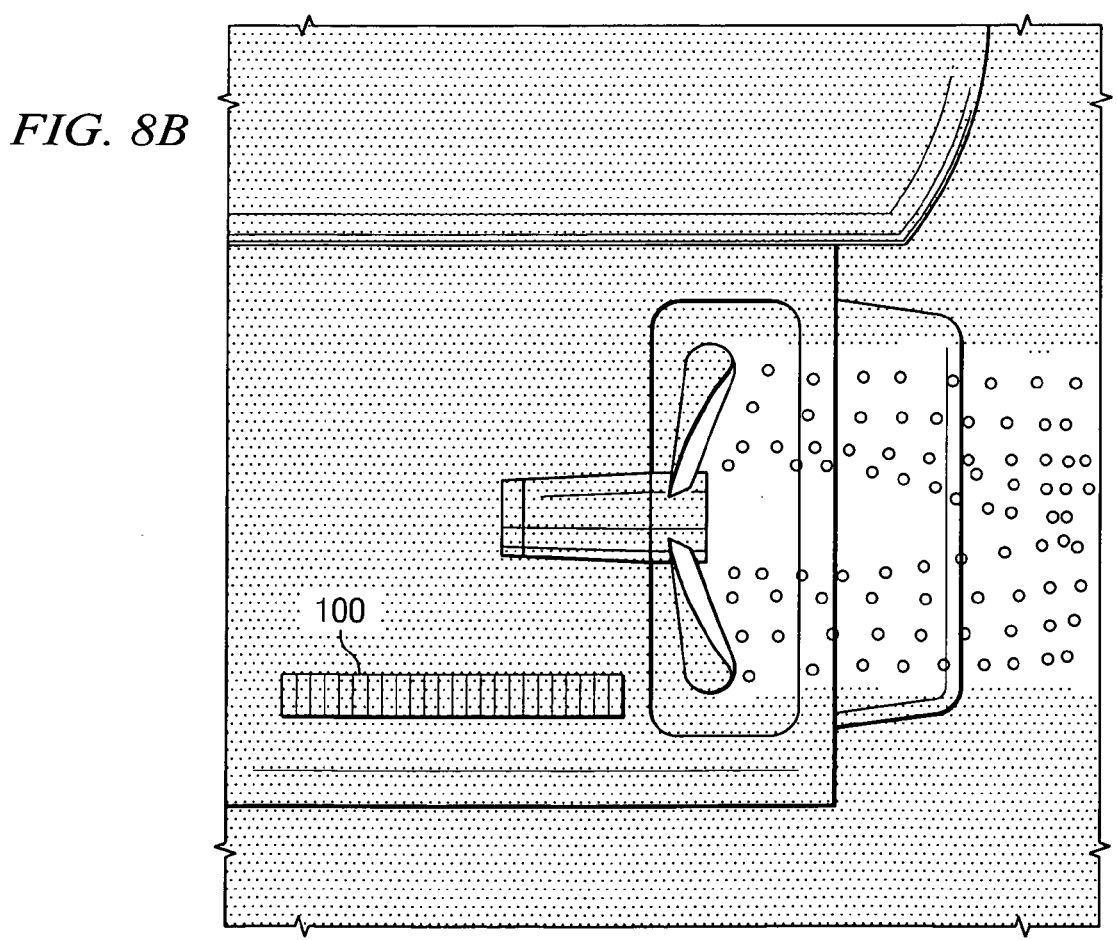

FIG. 8 depicts a more specific application of propulsor array 100 to large marine vessels. Because such vessels generally are designed for thrust applied near the aft bottom of the vessel, a first propulsor array is mounted on the vessel's port side and another on the starboard side, both in proximity to the vessel's propeller and rudder. Propulsor arrays 100 generally are placed below the propeller, but closely in front of the rudder, as shown in FIG. 8. The configuration depicted in FIG. 8 is particularly useful when a ship, such as vessel 800, needs to be propelled while completely empty of cargo, when the propeller is partially above the water line, and the propeller's efficiency reduced. This configuration also is of interest in cases where a ship needs to be propelled through waters full of foreign debris likely to be damaged by the propeller or damaging to the propeller. Typical scenarios include waters with dense vegetation, such as seaweed, or filled with floating pumice, ice, debris, or even people. FIG. 8B depicts the port side of vessel 800, on which one such propulsor array 100 is mounted. When activated, propulsor arrays 100 apply motion to the water, moving water towards the rear of vessel 800, thus moving vessel 800 forward. Propulsor arrays 100 also could have their synchronized motion reversed, moving water towards the front of vessel 800 and thus moving vessel 800 backwards.

Figure 9A:
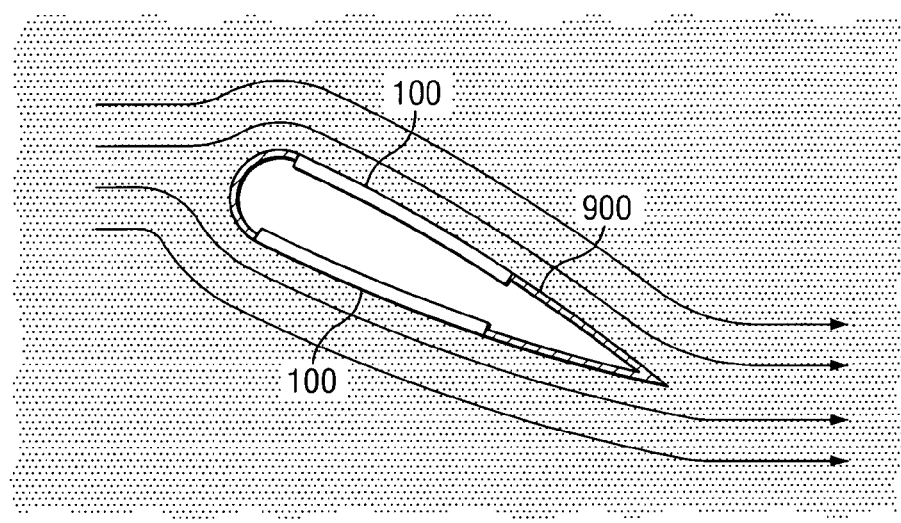
FIG. 9 illustrates an application of propulsor arrays to conventional control surfaces.
Figure 9B:
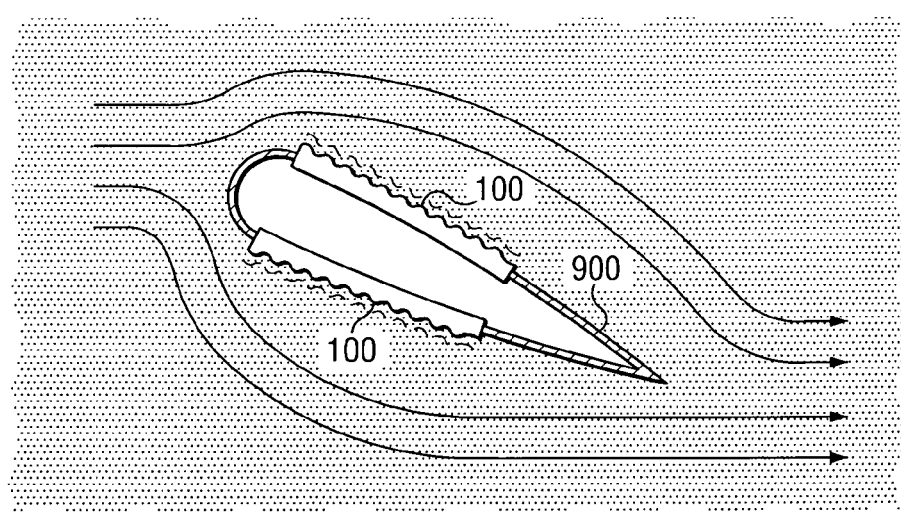

Propulsor arrays also are useful to modify the effectiveness of various conventional control surfaces, such as those illustrated in FIGS. 9A and 9B. FIGS. 9A and 9B depict two cross-sections through a conventional control surface (CCS) 900, such as a wing, rudder, stabilizer, bowplane, stemplane, or the like. In FIG. 9A, propulsor arrays 100 are inactive. The lines around CCS 900 illustrate the smooth flow of a fluid around CCS 900, which is inclined at an angle with respect to the flow of the fluid, such as when a rudder is used to turn a vessel by applying a force to the moving fluid or redirecting a portion of the moving fluid. In FIG. 9B, propulsor arrays 100 are active, creating a region of energized fluid around CCS 900 and increasing the effective size and power of CCS 900 in the fluid. The specific shape of each control surface 120 in FIG. 9B depends on the specific nature of the fluid and the larger maneuver that the vessel attached to CCS 900 is making. In one scenario, propulsor arrays 100 on both sides CCS 900 provide reverse thrust in order to maximize the drag of CCS 900 in the fluid. In another scenario, propulsor arrays 100 on either side of CCS 900 provide opposing motions to the fluid. ACS 510 also could provide different actions at different points in the cycle of the motion of CCS 900. FIG. 9 also shows another application of propulsors to wings and control elements, on which propulsor arrays 100 could be used to disrupt or induce laminar flow of a fluid across the wing. As a wing, FIG. 9B illustrates propulsor arrays 100 activated to disrupt laminar flow. Propulsor arrays 100 also could be activated with the appropriate wave motion in the fluid in order to induce a return to a laminar flow condition.

Figure 10A:
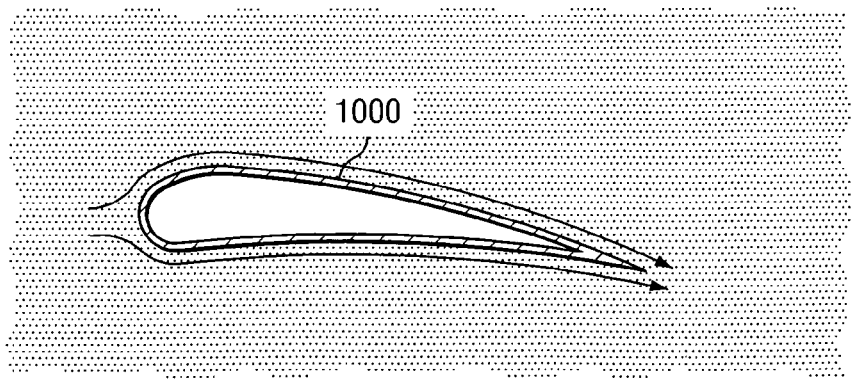
FIG. 10 illustrates an application of propulsor arrays to conventional airfoils.
Figure 10B:
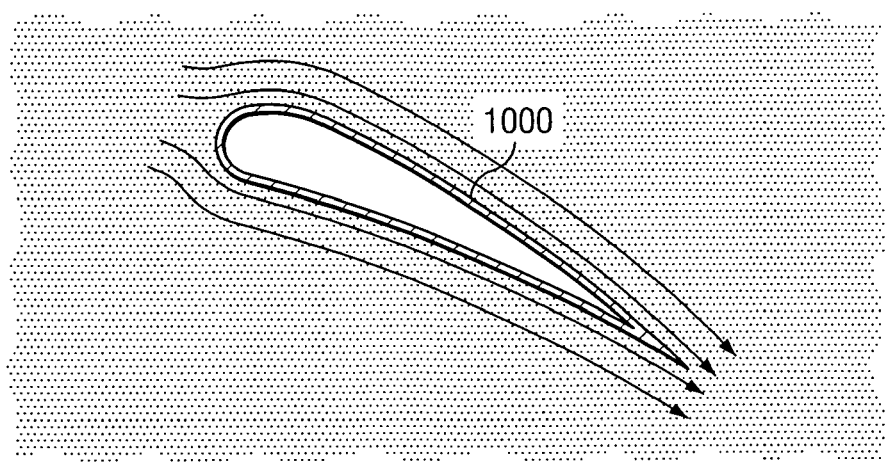
Figure 10C:
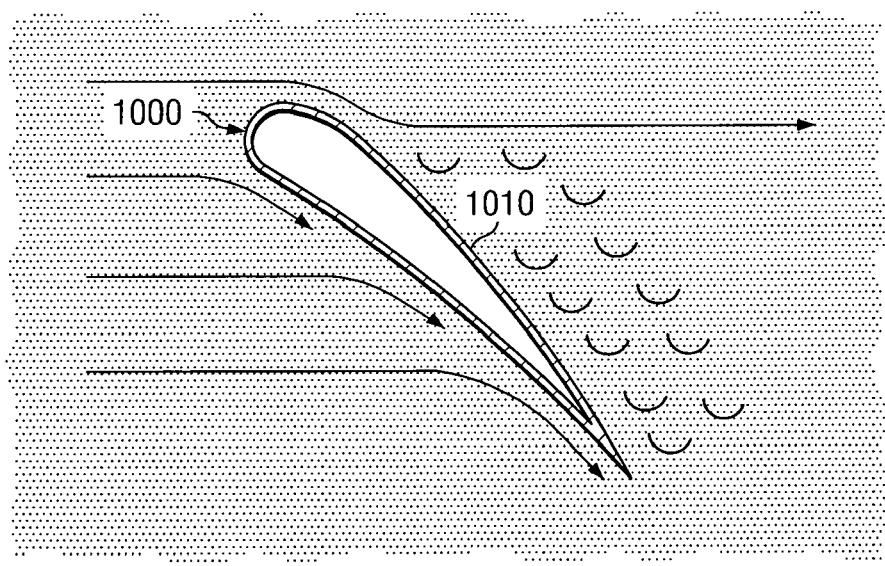
Figure 10D:
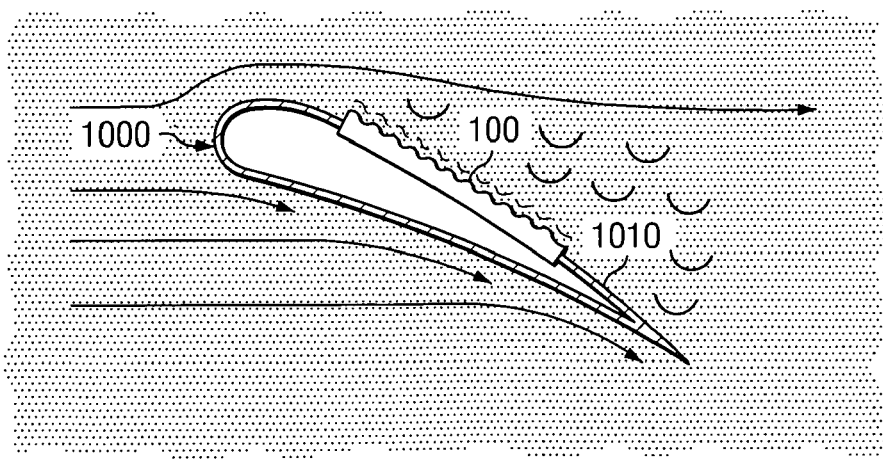

FIGS. 10A through 10D illustrate yet another application of propulsor arrays 100 to conventional airfoils operating in a gaseous fluid, such as air. FIGS. 10A through 10D each depict a cross-section of airfoil 1000 in a working fluid, such as air. FIGS. 10A through 10C illustrate an increased angle of attack (AOA) of airfoil 1000 embedded in a moving gas. At some angle that depends upon the specific shape of airfoil 1000 and the working fluid, airfoil 1000 stalls. At that specific angle, the smooth flow of the working fluid over top surface 1010 of airfoil 1000 is disrupted, and the lifting force of airfoil 1000 is severely diminished. A rectangular propulsor array 100 mounted on top surface 1010 allows a stall to be generated at will, especially at an AOA less than the angle usually required for a stall. In FIG. 10D, for instance, propulsor array 100 on top surface 1010 is active, providing disruptive energy to the airflow, disrupting the smooth flow of air over airfoil 1000, and generating a stall.

Figure 11A:
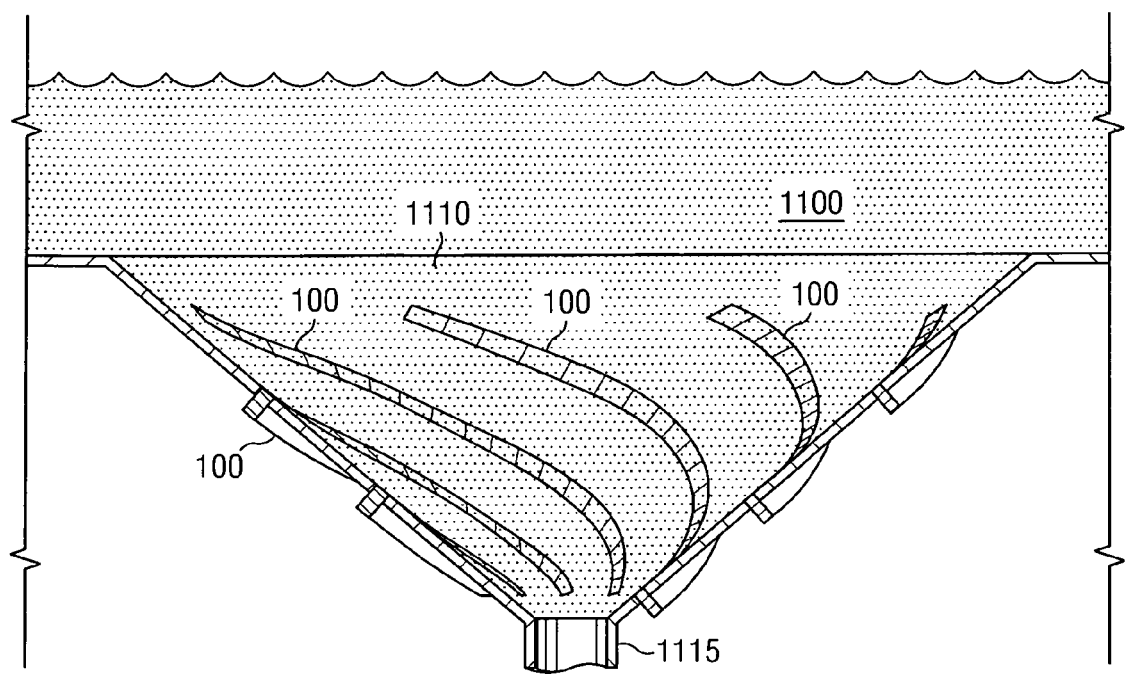
FIG. 11 illustrates propulsor arrays used to induce movement of a fluid into an intake mechanism.
Figure 11B:
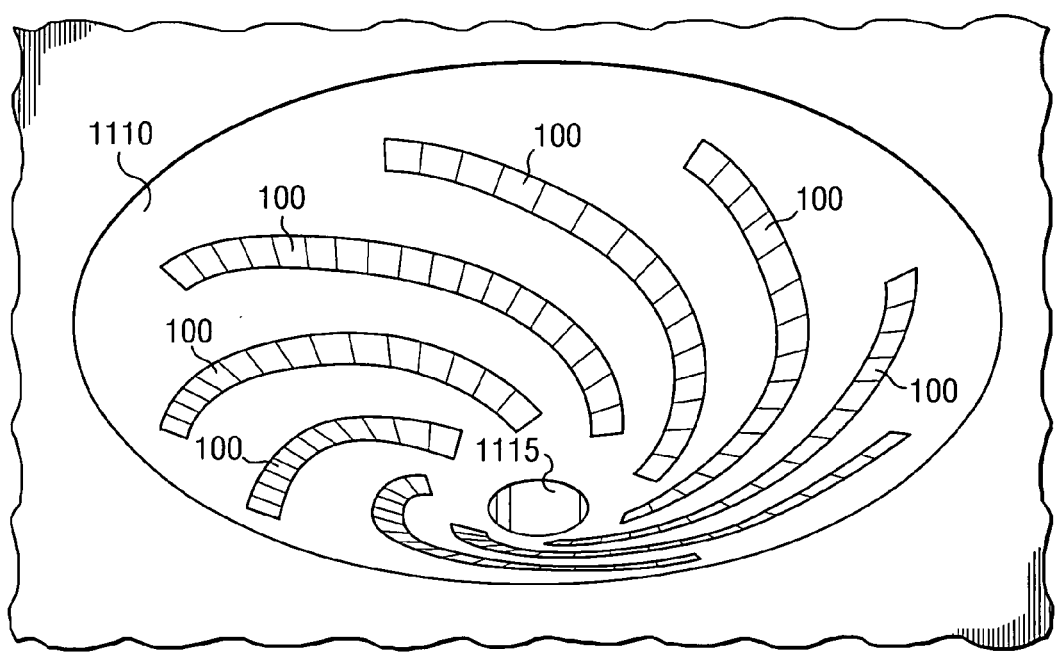

FIGS. 11A and 11B illustrate propulsor arrays used to induce movement of fluid into an intake mechanism. This application is useful for inducing fluid into a sensor in cases where conventional pumps are not appropriate. FIG. 11A is a cross-section view of device 1100 in contact with a working fluid. FIG. 11B is an overhead oblique view of device 1100. Device 1100 has conical orifice 1110 leading to the intake of plumbing or a sampling chamber. Propulsor arrays 100 are mounted in conical orifice 1110, radiating out from central intake 1115, to either induce motion in the fluid towards or away from central intake 1115.

Figure 12A:
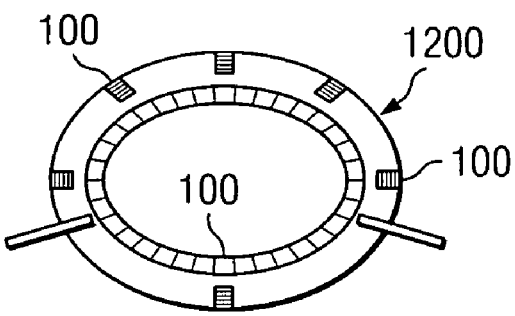
FIG. 12 illustrates an exemplary autonomous submersible device equipped with propulsor arrays.
Figure 12B:
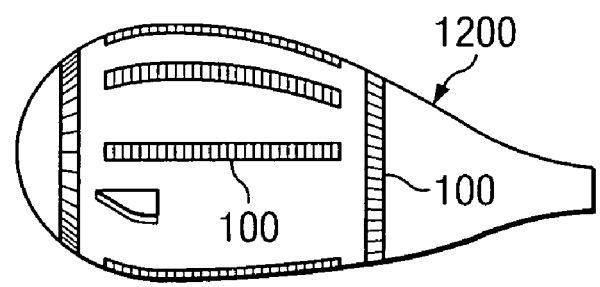
Figure 12C:
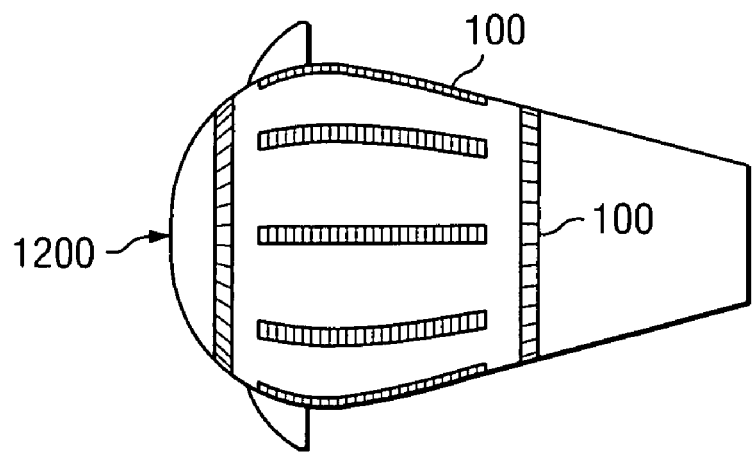

While applications for conventional marine vessels abound, propulsors are highly scalable and, thus, very useful as a propulsion mechanism in the developing field of micro- and nano-technology. In particular, these propulsors are ideal for autonomous submersible devices at this scale, such as exemplary miniature submarine 1200 depicted in FIGS. 12A through 12C. Miniature submarine 1200 uses propulsor arrays 100 for propulsion, orientation, and maneuvering. As FIGS. 12A through 12C illustrate, miniature submarine 1200 is a raindrop-device shaped device with a flattened tail. Several propulsor arrays 100 are arranged in the middle of the vessel to provide propulsion and maneuvering, thus leaving the front and rear of the device free for deploying sonar, cameras, sensors, manipulators, and towing loads. Since the midsection of miniature submarine 1200 is roughly spherical, propulsor arrays 100 are mounted to approximate lines of latitude and longitude. The latitudinal propulsors provide roll maneuvering and stability in turns. The longitudinal propulsors primarily generate propulsion. The top and bottom longitudinal propulsors also provide pitch maneuvering, while the side longitudinal propulsors provide yaw maneuvering.

A preferred form of the invention has been shown in the drawings and described above, but variations in the preferred form will be apparent to those skilled in the art. The preceding description is for illustration purposes only, and the invention should not be construed as limited to the specific form shown and described. The scope of the invention should be limited only by the language of the following claims.

What is claimed is:

1. A method of using a first propulsor array and a second propulsor array mounted on opposing surfaces of a submersible device to move and navigate the submersible device forward through a working fluid by generating thrust on the submersible device, wherein the submersible device has a bow and a stern, and each propulsor array comprises a substantially continuous control surface formed by a plurality of propulsors acting in concert to form the substantially continuous control surface, each propulsor having a bar, a first actuator coupled to the bar, a tip opposite the first actuator, and a second actuator adapted to change a shape of the control surface by altering a configuration of the tip, the method comprising:
   determining an appropriate shape of each of the control surfaces for the working fluid;
   manipulating each of the plurality of control tips to create the appropriate shave for each of the control surfaces;
   generating a wave on the control surface of the first propulsor array that moves from the bow to the stern; and
   generating a wave on the control surface of the second propulsor array that moves from the bow to the stern.

2. A method of using a first propulsor array and a second propulsor array mounted on opposing surfaces of a submersible device to move and navigate the submersible device backwards through a working fluid by generating thrust on the submersible device, wherein the submersible device has a bow and a stern, and each propulsor array comprises a substantially continuous control surface formed by a plurality of propulsors acting in concert to form the substantially continuous control surface, each propulsor having a bar, a first actuator coupled to the bar, a tip opposite the first actuator, and a second actuator adapted to change a shape of the control surface by altering a configuration of the tip, the method comprising:
   determining an appropriate shape of each of the control surfaces for the working fluid;
   manipulating each of the plurality of control tips to create the appropriate shape for each of the control surfaces;
   generating a wave on the control surface of the first propulsor array that moves from the stern to the bow; and
   generating a wave on the control surface of the second propulsor array that moves from the bow to the stern.

3. A method of using a first propulsor array and a second propulsor array mounted on opposing surfaces of a submersible device to orient the submersible device in a working fluid by generating a yaw force or a pitch force on the submersible device, wherein the submersible device has a bow and a stern, and each propulsor array comprises a substantially continuous control surface formed by a plurality of propulsors acting in concert to form the substantially continuous control surface, each propulsor having a bar, a first actuator coupled to the bar, a tip opposite the first actuator, and a second actuator adapted to change a shape of the control surface by altering a configuration of the tip, the method comprising:
   determining an appropriate shape of each of the control surfaces for the working fluid;
   manipulating each of the plurality of control tips to create the appropriate shape for each of the control surfaces;
   generating a wave on the control surface of the first propulsor array that moves from the bow to the stern; and
   generating a wave on the control surface of the second propulsor array that moves from the stern to the bow.

4. A method of using a propulsor array mounted circumferentially on the surface of a submersible device to orient the submersible device in a working fluid by generating a toll force on the submersible device, wherein the propulsor array comprises a substantially continuous control surface formed by a plurality of propulsors acting in concert to form the substantially continuous control surface, each propulsor having a bar, a first actuator coupled to the bar, a tip opposite the first actuator, and a second actuator adapted to change a shape of the control surface by altering a configuration of the tip, the method comprising generating a wave on the control surface of the first propulsor array that moves clockwise around the surface of the submersible device in response to a first manipulation of each of the bars by each of the first actuators and a second manipulation of each of the tips by each of the second actuators.

5. A method of using a propulsor array mounted circumferentially on the surface of a submersible device to orient the submersible device in a working fluid by generating a roll force on the submersible device, wherein the propulsor array comprises a substantially continuous control surface on formed by a plurality of propulsors acting in concert to form the substantially continuous control surface, each propulsor having a bar, a first actuator coupled to the bar, a tip opposite the first actuator, and a second actuator adapted to change a shape of the control surface by altering a configuration of the tip, the method comprising generating a wave on the control surface of the propulsor array that moves counter-clockwise around the surface of the submersible device in response to a first manipulation of each of the bars by each of the first and a second manipulation of each of the tips by each of the second actuators.

6. A method of using a propulsor array mounted circumferentially on the surface of a submersible device to move the submersible device vertically in a working fluid by generating a lift force on the submersible device, wherein the propulsor array comprises a substantially continuous control surface formed by a plurality of propulsors acting in concert to form the substantially continuous control surface, each propulsor having a bar, a first actuator coupled to the bar, a tip opposite the first actuator, and a second actuator adapted to change a shape of the control surface by altering a configuration of the tip, the method comprising:

responsive to a first manipulation of each of the bars by each of the first actuators and a second manipulation of each of the tips by each of the second actuators, generating a wave on a first half of the control surface that moves clockwise around the surface of the submersible device; and generating a wave on a second half of the control surface that moves counter-clockwise around the surface of the submersible device.

7. The method of claim 1 further comprising:

generating a wave train across the control surface capable of generating the wave so that the wave train speed is independent of a wavelength of the wave.

8. The method of claim 2 further comprising:

generating a wave train, across the control surface capable of generating the wave so that the wave train speed is independent of a wavelength of the wave.

9. The method of claim 3 further comprising:

generating a wave train across the control surface capable of generating the wave so that the wave train speed is independent of a wavelength of the wave.

10. The method of claim 4 further comprising:

generating a wave train across the control surface capable of generating the wave so that the wave train speed is independent of a wavelength of the wave.

11. The method of claim 5 further comprising:

generating a wave train across the control surface capable of generating the wave so that the wave train speed is independent of a wavelength of the wave.

12. The method of claim 6 further comprising:

generating a wave train across the control surface capable of generating the wave so that the wave train speed is independent of a wavelength of the wave.

* * * * *

UNITED STATES PATENT AND TRADEMARK OFFICE
CERTIFICATE OF CORRECTION

PATENT NO. : 7,090,548 B1
APPLICATION NO. : 11/050593
DATED : August 15, 2006
INVENTOR(S) : Gusler It is certified that error appears in the above-identified patent and that said Letters Patent is hereby corrected as shown below:

Col. 11, line 45: "shave" should be -- shape--

Col. 12, line 31: "toll" should be --roll--

Col. 12, line 49: delete "on"

Col. 12, line 58: insert --actuator-- after "first"

Signed and Sealed this

Twenty-second Day of May, 2007

JON W. DUDAS
*Director of the United States Patent and Trademark Office*